United States Patent [19]

Kobayashi et al.

[11] Patent Number: 5,210,237
[45] Date of Patent: May 11, 1993

[54] VITAMIN $D_3$ ANALOGUES

[75] Inventors: Yoshiro Kobayashi, Tokyo; Katsuhiko Iseki; Tadabumi Nagai, both of Tsukuba, all of Japan; Yoko Tanaka, Delmar, N.Y.; Nobuo Ikekawa, Musashino, Japan

[73] Assignee: Daikin Industries, Ltd., Osaka, Japan

[21] Appl. No.: 750,307

[22] Filed: Aug. 27, 1991

[51] Int. Cl.$^5$ .............................. C07J 9/00
[52] U.S. Cl. .................................. 552/653
[58] Field of Search ......................... 552/653

[56] References Cited

U.S. PATENT DOCUMENTS 4,853,378 8/1989 Hamma et al. .................. 552/653
4,973,721 11/1990 Ikekawa ........................ 552/653

OTHER PUBLICATIONS

K. W. Colston et al, "Lancet", Jan. 28, 1988, 1989.

Primary Examiner—Marianne M. Cintins
Assistant Examiner—Rebecca Cook
Attorney, Agent, or Firm—Birch, Stewart, Kolasch & Birch

[57] ABSTRACT

Vitamin $D_3$ analogues of the formula:

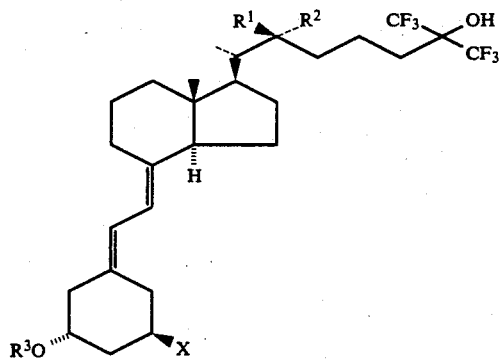

wherein $R^1$ is hydrogen atom and $R^2$ is hydroxy, or $R^1$ is hydroxy and $R^2$ is hydrogen atom, X is hydrogen atom, hydroxy or a hydroxy protected by a hydroxy-protecting group, and $R^3$ is hydrogen atom or a hydroxy-protecting group, which have vitamin $D_3$-like activities such as activity of controlling calcium metabolism and tumor cell differentiation-inducing activity.

9 Claims, No Drawings

VITAMIN D₃ ANALOGUES

This invention relates to novel vitamin D3 analogues having activity of calcium control in biobody and tumor cell differentiation-inducing activity.

Prior Art

It is known that a bio-metabolite of vitamin D3, 1α,25-dihydroxyvitamin D3 is called an "active-type vitamin D3" and has an activity of promoting absorption of calcium via intestinal tract and thereby is useful as a medicament for the treatment of bone diseases. Recently, it has been found that the active-type vitamin D3 and analogues thereof have a differentiation-inducing activity for recovering normal cells from cancerated cells (cf. Hirobumi Tanaka et al., "Seikagaku" (Biochemistry), Vol. 55, 1323, 1983) and further that some of these compounds have a remarked activity of inhibiting the progress of cancer (K. W. Colton et al., Lancet, Jan. 28, 188, 1989). It has, however, been known that these active-type vitamin D compounds have high antagonistic activity against calcium metabolism which is an undesirable side effect when used as an anti-tumor drug.

It is described in Japanese Patent First Publication (Kokai) No. 68528/1991 that novel vitamin D derivatives of the following formula have vitamin D-like activities.

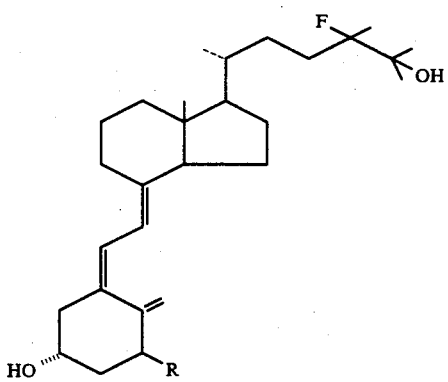

wherein R is hydrogen atom or hydroxy.

SUMMARY DESCRIPTION OF THE INVENTION

The present inventors have intensively studied as to novel vitamin D3 analogues which have excellent activities against calcium metabolism and cell differentiation.

An object of the invention is to provide novel vitamin D3 analogues having pharmacological activities, especially anti-tumor activity owing to the cell differentiation-inducing activity. Another object of the invention is to provide a process for preparing the vitamin D3 analogue. These and other objects and advantages of the invention will be apparent to the skilled persons in this field from the following description.

DETAILED DESCRIPTION OF THE INVENTION

The vitamin D3 analogues of this invention have the following formula [I]:

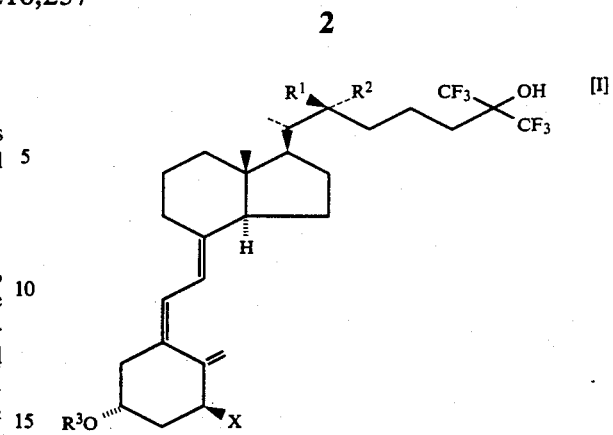

wherein $R^1$ is hydrogen atom and $R^2$ is hydroxy, or $R^1$ is hydroxy and $R^2$ is hydrogen atom, X is hydrogen atom, hydroxy or a hydroxy protected by a hydroxy-protecting group, and $R^3$ is hydrogen atom or a hydroxy-protecting group.

In the present specification and claims, the hydroxy-protecting group includes a silyl ether type protecting group such as trimethylsilyl, t-butyldimethylsilyl, t-butyldiphenylsilyl, and the like.

Suitable examples of the compounds [I] are as follows.

26,26,26,27,27,27-Hexafluoro-24-homo-22,25-dihydroxyvitamin D3 (Compound A)
26,26,26,27,27,27-hexafluoro-24-homo-1α,22,25-trihydroxyvitamin D3 (Compound B)
3-Trimethylsilyl ether of Compound A
3-t-Butyldimethylsilyl ether of Compound A
3-t-Butyldiphenylsilyl ether of Compound A
1α,3-Bis(trimethylsilyl) ether of Compound B
1α,3-Bis(t-butyldimetylsilyl) ether of Compound B
1α,3-Bis(t-butyldiphenylsilyl)ether of Compound B The compounds [I] of this invention can be prepared by various processes. One of the best processes is illustrated below.

A ketone compound of the formula [II]:

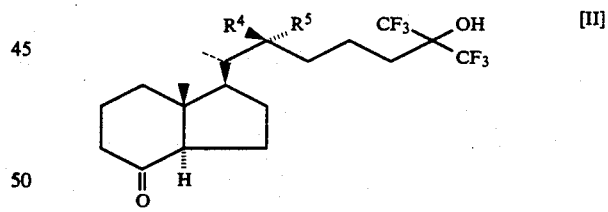

wherein $R^4$ is a group of the formula: $OR^6$ and $R^5$ is hydrogen atom, or $R^5$ is a group of the formula: $OR^6$ and $R^4$ is hydrogen atom, and $R^6$ is a hydroxy-protecting group, is subjected to coupling reaction with an anion derived from a phosphine oxide of the formula [III]:

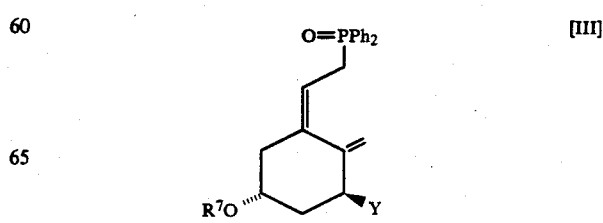

wherein $R^7$ is a hydroxy-protecting group, Y is hydrogen atom or a group of the formula: $OR^7$, and Ph means phenyl, optionally followed by removing the hydroxy-protecting group. The derivation of phosphine oxide to the anion is carried out in the presence of a base such as alkyllithium (e.g. n-butyllithium).

The above coupling reaction of the compound [II] and the compound [III] is usually carried out at a low temperature, for example $-100°$ C. to $-50°$ C., preferably $-80°$ to $-20°$ C., under an inert atmosphere (e.g. under argon gas) in an ether solvent (e.g. diethyl ether, tetrahydrofuran (THF), etc.) for 10 minutes to 24 hours, preferably for 30 minutes to 2 hours. The obtained product [I]can be purified by a conventional method, for example, by silica gel chromatography. The removal of the hydroxy-protecting group from the compound [I] can be carried out by a conventional method.

The hydroxy-protecting group $R^6$ in the formula [II] is preferably a silyl group (e.g. t-butyldimethylsilyl, etc.) or an acyl group (e.g. acetyl, etc.). The hydroxy-protecting group $R^7$ in the formula [III] is preferably a silyl group (e.g. t-butyldimethylsilyl etc.).

The starting compound [III] used in the above coupling reaction is prepared by a known process as disclosed in E. G. Baggiolini et al., *J. Am. Chem. Soc.*, Vol. 104, 2945, 1982 and Japanese Patent First Publication (Kokai) No. 250844/1990.

On the other hand, another starting compound [II] can be prepared by the process as illustrated by the following reaction scheme:

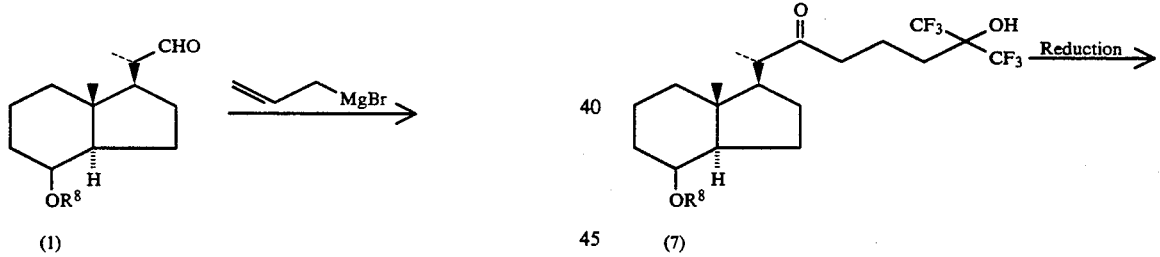

(1)

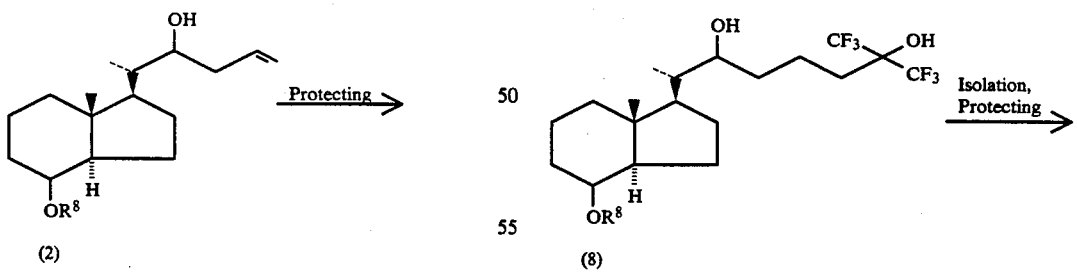

(2)

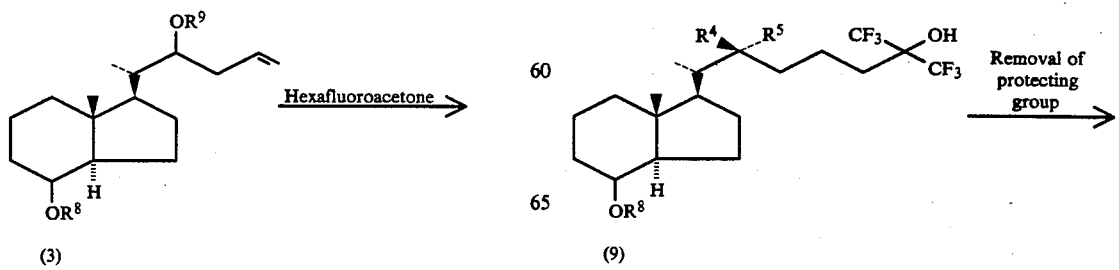

(3)

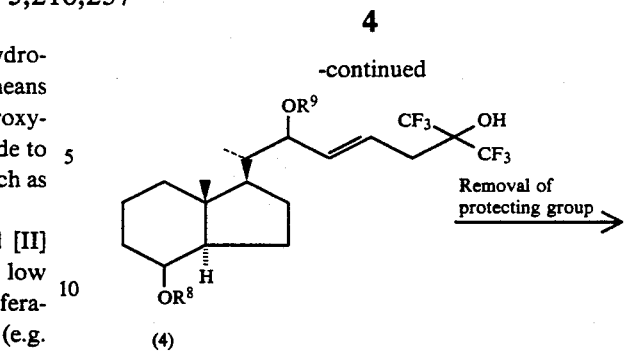

(4)

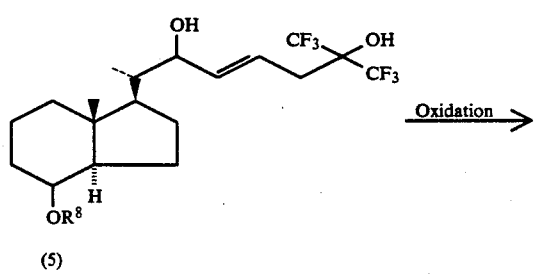

(5)

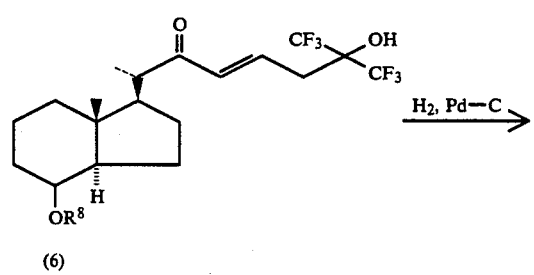

(6)

(7)

(8)

(9)

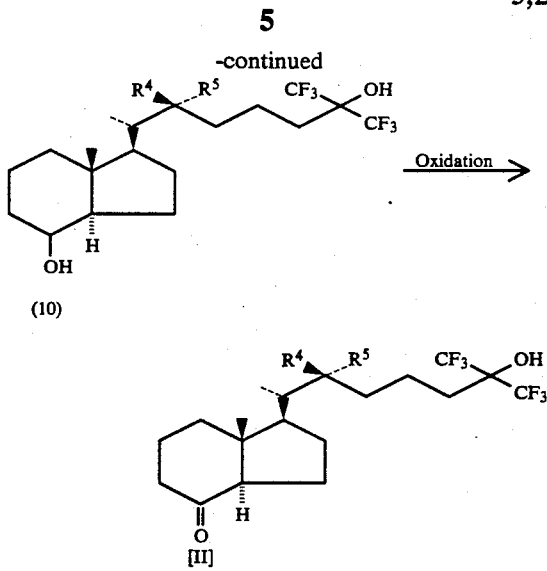

(10)

[II]

wherein $R^4$ and $R^5$ are as defined above, and $R^8$ and $R^9$ are each a hydroxy-protecting group.

According to the above process, the starting compound [II] can be prepared by reacting the aldehyde compound (1) with a Grignard reagent to give the compound (2), protecting the hydroxy group of the compound (2) with a hydroxy-protecting group in a usual manner, reacting the resultant compound (3) with hexafluoroacetone, removing the hydroxy-protecting group $R^9$ from the resultant compound (4), oxidizing the resultant compound (5), hydrogenating the resultant compound (6) in the presence of palladium-carbon, further reducing the resultant compound (7), isolating the resultant compound (8) and then protecting the hydroxy group thereof, removing the hydroxy-protecting group of the resultant compound (9), and finally oxidizing the compound (10). The detail conditions of the above process are illustrated by Reference Examples 1 to 10 hereinafter.

The compounds of this invention are illustrated by the following Examples and Reference Examples, but should not be construed to be limited thereto.

EXAMPLE 1

1-1. Preparation of 1α,3,22-tris(t-butyldimethylsilyl) ether of 26,26,26,27,27,27-hexafluoro-24-homo-1α,22,25-trihydroxyvitamin $D_3$ (Compound B) by Wittig reaction of compound [II] and compound [III]:

To a solution of a compound of the formula (III) wherein $R^7$ is t-butyldimethylsilyl and Y is t-butyldimethylsilyloxy (320 mg) in anhydrous THF (8 ml) is added dropwise n-butyllithium (2.5M, in the form of a solution in hexane) at −78° C., and the mixture is stirred at the same temperature for 5 minutes. To the mixture is added a solution of the compound (II) wherein $R^4$ is t-butyldimethylsilyloxy and $R^5$ is hydrogen atom (27 mg) in anhydrous THF (1 ml) at one time. The mixture is warmed to room temperature and then is stirred for 10 minutes. The reaction mixture is added to saturated aqueous ammonium chloride solution and is extracted with ethyl acetate. The ethyl acetate layer is washed with water and dried over anhydrous magnesium sulfate. After distilling off the solvent, the residue is purified by column chromatography (SiO$_2$, eluant, n-hexane ethyl acetate=20:1) to give the title compound (28.3 mg, 63.2%) as colorless viscous substance.

$^1$H-NMR (CDCl$_3$) δ: 0.03 (3H, s), 0.06 (6H, s), 0.54 (3H, s), 0.83–0.93 (3H, m), 0.88 (9H, s), 0.88 (9H, s), 0.89 (9H, s), 1.12–2.08 (19H, m), 2.21 (1H, d-d, J=13.8, 7.4 Hz), 2.45 (1H, d-d, J=13.8, 4.7 Hz), 2.75–2.90 (1H, m), 3.02 (1H, bs), 3.55–3.77 (1H, m), 4.10–4.27 (1H, m), 4.33–4.45 (1H, m), 4.85–4.90 (1H, m), 5.17–5.23 (1H, m), 6.02 (1H, d, J=11.4 Hz), 6.24 (1H, d, J=11.4 Hz)

IR (neat): 3416, 2930 cm$^{-1}$ 1-2. Preparation of Compound B by removal of the protecting silyl group:

To a solution of the tris(t-butyldimethylsilyl) ether of Compound (B) obtained in Example 1-1 (26.3 mg) in anhydrous THF (1 ml) is added dropwise a solution (0.3 ml) of tetra(n-butyl)ammonium fluoride in THF (1M) at room temperature, and the mixture is stirred at room temperature for 12.5 hours. The reaction mixture is added to saturated aqueous ammonium chloride solution and is extracted with ethyl acetate. The organic layer is washed with water and dried over anhydrous magnesium sulfate. After distilling off the solvent, the residue is purified by column chromatography (SiO$_2$, eluant, n-hexane-ethyl acetate=1:1) to give the Compound (B) (15.58 mg, 95.8%) as colorless needles.

$^1$H-NMR (CD$_3$OD) δ: 0.58 (3H, s), 0.92 (3H, d, J=6.5 Hz), 1.20–2.35 (20H, m), 2.40–2.62 (1H, m), 2.75–2.95 (1H, m), 3.60–3.78 (1H, m), 4.00–4.25 (1H, m), 4.25–4.45 (1H, m), 4.57 (1H, bs), 4.90–5.00 (1H, m), 5.27–5.34 (1H, m), 6.09 (1H, d, J=11.2 Hz), 6.33 (1H, d, J=11.2 Hz)

IR (KBr): 3420, 2940 cm$^{-1}$

EXAMPLE 2

Preparation of 26,26,26,27,27,27-hexafluoro-24-homo-22,25-dihydroxyvitamin $D_3$ (Compound A):

In the same manner as described in Example 1, there is prepared Compound A (yield 62.0%) as colorless powder.

$^1$H-NMR (CD$_3$OD) δ: 0.56 (3H, s), 0.91 (3H, d, J=6.7 Hz), 1.20–2.60 (24H, m), 2.85 (1H, m), 3.65 (1H, m), 3.76 (1H, m), 4.74 (1H, bs), 5.03 (1H, bs), 6.03 (1H, d, J=11.0 Hz), 6.22 (1H, d, J=11.0 Hz)

IR (KBr): 3374, 2947, 1211, 1047 cm$^{-1}$

REFERENCE EXAMPLE 1

Preparation of Compound (2) wherein $R^8$ is benzyl by subjecting Compound (1) to Grignard reaction:

To a solution of Compound (1) wherein $R^8$ is benzyl (327 mg) in anhydrous diethyl ether (3 ml) is added dropwise allylmagnesium bromide-THF solution (2M, 2 ml) at 0° C., and the mixture is stirred for one hour. The reaction mixture is poured into saturated aqueous ammonium chloride solution and extracted with diethyl ether. The ether layer is washed with water and dried over anhydrous magnesium sulfate. After distilling off the solvent, the residue is purified by column chromatography (SiO$_2$, eluant: n-hexane-methylene chloride=1:1) to give two diastereomers, Compound (2-1) (176 mg, 47.2%) and Compound (2-2) (147 mg 39.4%).

The Compound (2-1) has the following physical properties:

Colorless oil, $^1$H-NMR (CDCl$_3$) δ: 0.92 (3H, d J=5.9 Hz), 0.97 (3H s), 1.10–2.40 (16H, m), 3.64–3.80 (2H, m), 4.36 (1H, d, J=12.3 Hz), 5.02–5.21 (2H, m), 5.64–5.87 (1H, m), 7.17–7.50 (5H, m), IR (neat): 3421, 2938, 2865 cm$^{-1}$ The Compound (2-2) has the following physical properties:

Colorless oil, $^1$H-NMR (CDCl$_3$) δ: 0.93 (3H, d, J=6.8 Hz), 0.99 (3H, s), 1.00–2.29 (16H, m), 3.64–3.78 (2H, m), 4.36 (1H, d, J=12.4 Hz), 4.63 (1H, d, J=12.4 Hz), 5.03–5.21 (2H, m), 5.66–6.00 (1H, m), 7.18–7.42 (5H, m), IR (neat): 3406, 2937, 2864 cm$^{-1}$

REFERENCE EXAMPLE 2

Preparation of Compound (3) wherein R$^8$ is benzyl and R$^9$ is acetyl by acetylation of Compound (2):

A mixture of Compound (2-1) obtained in Reference Example 1 (176 mg), acetic anhydride (204 mg) and pyridine (1 ml) is stirred at room temperature for 13 hours. The reaction mixture is extracted with diethyl ether and the ether layer is washed with diluted hydrochloric acid, saturated sodium hydrogen carbonate solution, and saturated saline solution in this order, and dried over anhydrous magnesium sulfate. After distilling off the solvent, the residue is purified by column chromatography (SiO$_2$, eluant, n-hexane-methylene chloride=2:1) to give Compound (3) (185 mg, 94.5%).

The Compound (3) has the following physical properties:

Colorless oil, $^1$H-NMR (CDCl$_3$) δ: 0.96 (3H, s), 0.97 (3H, d, J=6.4 Hz), 1.05–2.09 (14H, m), 2.03 (3H, s), 2.20 (1H, d-d-d, J=7.0, 7.0, 13.0 Hz), 2.39 (1H, d-d-d, J=7.0, 7.0, 13.0 Hz), 3.66–3.73 (1H, m), 4.35 (1H, d, J=12.3 Hz), 4.61 (1H, d, J=12.3 Hz), 4.97–5.14 (2H, m), 5.59–5.83 (1H, m), 7.17–7.38 (5H, m), IR (neat): 2940, 2867, 1735 cm$^{-1}$

REFERENCE EXAMPLE 3

Preparation of Compound (4) wherein R$^8$ is benzyl and R$^9$ is acetyl by reacting Compound (3) with hexafluoroacetone:

To a solution of Compound (3) obtained in Reference Example 2 (1.20 g) in benzene (10 mg) is added hexafluoroacetone (1 ml) in a stainless steel autoclave, and the mixture is heated at 150° C. for 39 hours. After allowing to cool, the reaction mixture is extracted with diethyl ether. After distilling off the solvent, the residue is purified by column chromatography (SiO$_2$, eluant, n-hexane-ethyl acetate=10:1) to give Compound (4) (1.267 g, 73.7%).

The Compound (4) has the following physical properties:

Colorless needles,

M.p. 134.8°–135.9° C., $^1$H-NMR (CDCl$_3$) δ: 0.96 (3H, d, J=6.7 Hz), 0.96 (3H, s), 1.08–2.11 (14H, m), 2.08 (3H, s), 2.71 (1H, d, J=7.2 Hz), 3.41 (1H, s), 3.65–3.80 (1H, m), 4.35 (1H, d, J=12.3 Hz), 4.61 (1H, d, J=12.3 Hz), 5.50 (1H, d-t, J=15.6, 5.1 Hz), 5.71 (1H, d-d, J=15.6, 5.2 Hz), 7.19–7.40 (5H, m),

IR (KBr): 3364, 2932, 1720 cm$^{-1}$

REFERENCE EXAMPLE 4

Preparation of Compound (5) wherein R$^8$ is benzyl by hydrolysis of Compound (4):

A solution of Compound (4) obtained in Reference Example 3 (1.195 g) and potassium carbonate (1.38 g) in methanol (15 ml) is stirred at room temperature for 48 hours. The reaction mixture is poured into water and is extracted with diethyl ether. The ether layer is washed with water and dried over anhydrous magnesium sulfate. After distilling off the solvent, the residue is purified by column chromatography (SiO$_2$, eluant, n-hexane-ethyl acetate=2:1) to give Compound (5) (1.0186 g, 92.4%).

The Compound (5) has the following physical properties:

Colorless needles,

M.P. 130.0°–130.5° C., $^1$H-NMR (CDCl$_3$) δ: 0.87 (3H, d, J=6.4 Hz), 0.97 (3H, s), 1.06–2.10 (14H, m), 2.73 (2H, d, J=7.5 Hz), 3.26 (1H, bs), 3.69–3.78 (1H, m), 4.33 (1H, bs), 4.36 (1H, d, J=12.3 Hz), 4.63 (1H, d, J=12.3 Hz), 5.66 (1H, d-t, J=15.5, 7.5 Hz), 5.79 (1H, d-d, J=15.5, 3.7 Hz), 7.18–7.44 (5H, m),

IR (KBr): 3535, 3114,.2945 cm$^{-1}$

REFERENCE EXAMPLE 5

Preparation of Compound (6) wherein R$^8$ is benzyl by oxidation of Compound (5):

To a mixture of pyridine (2.4 g) and anhydrous methylene chloride (15 ml) is added chromium trioxide (1.2 g) under argon gas at room temperature, and the mixture is stirred for 15 minutes. To the mixture is added Compound (5) obtained in Reference Example 4 under argon gas, and the mixture is stirred at room temperature for 10 minutes. The supernatant of the reaction mixture is taken by decantation, and the residue is washed with diethyl ether. The combined organic layer is washed with water, and dried over anhydrous magnesium sulfate. After distilling off the solvent, the residue is purified by column chromatography (SiO$_2$, eluant, n-hexane-ethyl acetate=10:1) to give Compound (6) (963 mg, 96%).

The Compound (6) has the following physical properties:

Colorless oil, $^1$H-NMR (CDCl$_3$) δ: 1.00 (3H, s), 1.11 (3H, d, J=6.9 Hz), 1.00–2.10 (12H, m), 2.73 (1H, q-d, J=6.9, 9.9 Hz), 2.86 (2H, d, J=7.6 Hz), 3.68–3.78 (1H, m), 4.35 (1H, d, J=12.3 Hz), 4.48 (1H, bs), 4.61 (1H, d, J=12.3 Hz), 6.31 (1H, d, J=15.6 Hz), 6.89 (1H, d-t, J=15.6, 7.6 Hz), 7.20–7.43 (5H, m), IR (neat): 3299, 2936, 1686, 1660 cm$^{-1}$

REFERENCE EXAMPLE 6

Preparation of Compound (7) wherein R$^8$ is benzyl by reduction of Compound (6):

The Compound (6) obtained in Reference Example 5 (464 mg) is stirred under hydrogen gas in the presence of 5% Pd-C catalyst (20 mg) in methanol (20 ml) for 1 hour. After removing the catalyst by filtration and distilling off the solvent, the residue is purified by column chromatography (SiO$_2$, eluant, n-hexane-ethyl acetate=5:1) to give Compound (7) (466.7 mg, 96%).

The Compound (7) has the following physical properties:

Colorless oil, $^1$H-NMR (CDCl$_3$) δ: 0.98 (3H, s), 1.09 (3H, d, J=6.8 Hz), 1.05–2.12 (16H, m), 2.40–2.78 (4H, m), 3.68–3.77 (1H, m), 4.35 (1H, d, J=12.3 Hz), 4.62 (1H, d, J=12.3 Hz), 7.20–7.45 (5H, m), IR (neat): 3283, 2936, 1694 cm$^{-1}$

REFERENCE EXAMPLE 7

Preparation of Compound (8) wherein R$^8$ is benzyl by reduction of Compound (7):

To a solution of Compound (7) obtained in Reference Example 6 (466.7 mg) in ethanol (1 ml) is added sodium borohydride (33.4 mg), and the mixture is stirred at room temperature for 2.5 hours. The reaction mixture is poured into ice-water and extracted with diethyl ether and the ether layer is washed with water and dried over anhydrous magnesium sulfate. After distilling off the solvent, the residue is purified by column chromatography (SiO$_2$, eluant, methylene chloride-acetonitrile=50:1) to give two diastereomers of Compound (8) (303 mg, 67%, and 104 mg, 23% respectively).

The main product of Compound (8) has the following physical properties:

Colorless needles,
M.p. 156.9°–157.6° C.,
$^1$H-NMR (CD$_3$COCD$_3$) δ: 0.91 (3H, d, J=6.5 Hz), 0.97 (3H, s), 1.10–2.13 (19H, m), 3.24 (1H, d, J=5.6 Hz), 3.60–3.80 (2H, m), 4.35 (1H, d, J=12.3 Hz), 6.54 (1H, s), 7.14–7.45 (5H, m),
IR (KBr): 3536, 2942 cm$^{-1}$ The other isomer of Compound (8) has the following physical properties:

Colorless needles,
M.p. 142.3°–144.0 ° C.,
$^1$H-NMR (CD$_3$CN) δ: 0.87 (3H, d, J=6.7 Hz), 0.94 (3H, s), 1.00–2.10 (19H, m), 2.87 (1H, d, J=4.4 Hz), 3.50–3.68 (1H, m), 3.68–3.80 (1H, m), 4.32 (1H, d, J=12.1 Hz , 4.59 (1H, d, J=12.1 Hz), 5.95 (1H, bs), 7.10–7.44 (5H, m),
IR (KBr): 3512 3156, 2932 cm$^{-1}$

REFERENCE EXAMPLE 8

Preparation of Compound (9) wherein R$^4$ is t-butyldimethylsilyl, R$^5$ is hydrogen atom and R$^8$ is benzyl by protecting Compound (8) with t-butyldimethylsilyl group:

To a solution of Compound (8) obtained in Reference Example 7 (164 mg) in anhydrous methylene chloride are added 2,6-lutidine (284 μl) and t-butyldimethylsilyl trifrate (267 μl), and the mixture is stirred at room temperature for 13 hours. The reaction mixture is poured into ice-water and extracted with methylene chloride. The methylene chloride layer is washed with water and dried over anhydrous magnesium sulfate. After distilling off the solvent, the residue is purified by column chromatography (SiO$_2$, eluant, n-hexane-methylene chloride=1:1) to give Compound (9) (200 mg, 100%).

The Compound (9) has the following physical properties:

Colorless viscous,
$^1$H-NMR (CDCl$_3$) δ: 0.03 (3H, s), 0.05 (3H, s), 0.88 (9H, s), 0.88 (3H, d, J=5.7 Hz), 0.96 (3H, s), 1.05–2.07 (20H, m), 3.05 (1H, s), 3.58–3.75 (2H, m), 4.36 (1H, d, J=12.4 Hz), 4.62 (1H, d, J=12.4 Hz), 7.19–7.43 (5H, m),
IR (neat): 3385, 2932, 2859 cm$^{-1}$

REFERENCE EXAMPLE 9

Preparation of Compound (10) wherein R$^4$ is t-butyldimethylsilyl and R$^5$ is hydrogen atom by removal of benzyl group from Compound (9) by hydrolysis:

The Compound (9) obtained in Reference Example 8 (200 mg) is stirred under hydrogen gas in the presence of Pd-C catalyst (10 mg) in methanol (10 ml) at room temperature and under atmospheric pressure for 13 hours. After removing the catalyst by filtration and concentrating the filtrate, the residue is purified by column chromatography (SiO$_2$, eluant, n-hexane-methylene chloride=5:1) to give Compound (10) (162 mg, 95%).

The Compound (10) has the following physical properties:

Colorless needles,
M.P. 116.1°–117.0° C.,
$^1$H-NMR (CDCl$_3$) δ: 0.03 (3H, s), 0.04 (3H, s), 0.85 (3H, d, J=6.1 Hz), 0.88 (9H, s), 0.92 (3H, s), 1.04–2.10 (20H, m), 3.56–3.71 (1H, m), 4.03–4.15 (1H, m), 4.27 (1H, bs)
IR (KBr): 3504, 2956, 1463 cm$^{-1}$

REFERENCE EXAMPLE 10

Preparation of Compound [II]wherein R$^4$ is t-butyldimethylsilyl and R$^5$ is hydrogen atom by oxidation of Compound (10):

A solution of Compound (10) obtained in Reference Example 9 (160 mg) in anhydrous methylene chloride is added dropwise to a suspension of pyridinium chlorochromate (216 mg) in anhydrous methylene chloride, and the mixture is stirred at room temperature for 2 hours. The reaction mixture is extracted with diethyl ether and the ether layer is washed with water and dried over anhydrous magnesium sulfate. After distilling off the solvent, the residue is purified by column chromatography (SiO$_2$, eluant, n-hexane-ethyl acetate =5 : 1) to give Compound [II] (152 mg, 95%).

The Compound [II]has the following physical properties:

Colorless needles,
M.p. 128.6°–130° C.,
$^1$H-NMR (CD OD) δ: 0.08 (3H, s) 0.09 (3H, s) 0.65 (3H, s), 0.91 (9H, s), 0.95 (3H, d, J=6.4 Hz), 1.20–2.63 (20H, m), 3.66–3.78 (1H, m),
IR (KBr): 3243, 2961, 1698 cm$^{-1}$

What is claimed is:

1. A vitamin D$_3$ analogue of the formula [I]:

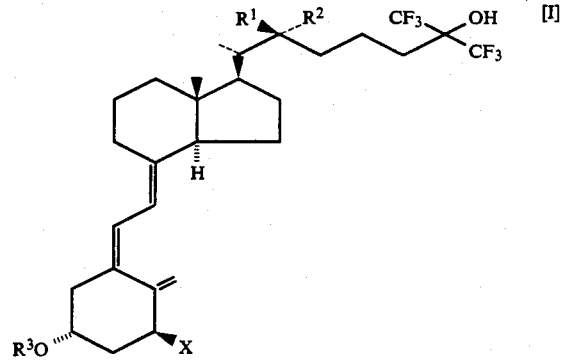

wherein R$^1$ is hydrogen atom and R$^2$ is hydroxy, or R$^1$ is hydroxy and R$^2$ is hydrogen atom, X is hydrogen atom, hydroxy or a hydroxy protected by a hydroxy-protecting group, and R$^3$ is hydrogen atom or a hydroxy-protecting group.

2. The compound according to claim 1, wherein the hydroxy-protecting group is selected from the group consisting of trimethylsilyl, t-butyldimethylsilyl and t-butyldiphenylsilyl.

3. The compound according to claim 1 which is a member selected from the following groups:
6,26,26,27,27,27-hexafluoro-24-homo-22,25-dihydroxyvitamin D$_3$,
26,26,26,27,27,27-hexafluoro-24-homo-1α,22,25-trihydroxyvitamin D$_3$,
3-trimethylsilyl ether of 26,26,26,27,27,27-hexafluoro-24-homo-22,25-dihydroxyvitamin D$_3$,
3-t-butyldimethylsilyl ether of 26,26,26,27,27,27-hexafluoro-24-homo-22,25-dihydroxyvitamin D$_3$, 3-t-butyldiphenylsilyl ether of 26,26,26,27,27,27-hexafluoro-24-homo-22,25-dihydroxyvitamin D$_3$, 1α, 3-bis(trimethylsilyl) ether of 26,26,26,27,27,27-hexafluoro-24-homo-1α,22,25-trihydroxyvitamin D$_3$, 1,α,3-bis(t-butyldimethylsilyl) ether of 26,26,26,27,27,27-hexafluoro-24-homo-1α,22,25-trihydroxyvitamin D$_3$, 1α,3-bis(t-butyldiphenylsilyl) ether of 26,26,26,27,27,27-hexafluoro-24-homo-1α,22,25-trihydroxyvitamin D$_3$.

4. The compound according to claim 1, wherein R$^1$ is a hydrogen atom and R$^2$ is hydroxy.

5. The compound according to claim 4, wherein the hydroxy-protecting group is selected from the group consisting of trimethylsilyl, t-butyldimethylsilyl and t-butyldiphenylsilyl.

6. The compound according to claim 1, wherein R$^1$ is hydroxy and R$^2$ is a hydrogen atom.

7. The compound according to claim 6, wherein the hydroxy-protecting group is selected from the group consisting of trimethylsilyl, t-butyldimethylsilyl and t-butyldiphenylsilyl.

8. The compound according to claim 3, wherein R$^1$ is a hydrogen atom and R$^2$ is hydroxy.

9. The compound according to claim 3, wherein R$^1$ is hydroxy and R$^2$ is a hydrogen atom.

* * * * *